(12) United States Patent
Nakagawa et al.

(10) Patent No.: US 9,833,329 B2
(45) Date of Patent: Dec. 5, 2017

(54) IMPLANT ASSEMBLY

(71) Applicant: TERUMO KABUSHIKI KAISHA, Tokyo (JP)

(72) Inventors: Yuji Nakagawa, Isehara (JP); Suguru Hata, Atsugi (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 21 days.

(21) Appl. No.: 14/873,702

(22) Filed: Oct. 2, 2015

(65) Prior Publication Data

US 2016/0022427 A1     Jan. 28, 2016

Related U.S. Application Data

(63) Continuation of application No. PCT/JP2013/060025, filed on Apr. 2, 2013.

(51) Int. Cl.
    *A61F 2/44*     (2006.01)
    *A61F 2/46*     (2006.01)
    (Continued)

(52) U.S. Cl.
    CPC .......... *A61F 2/441* (2013.01); *A61B 17/7065* (2013.01); *A61F 2/44* (2013.01);
    (Continued)

(58) Field of Classification Search
    CPC .............. A61F 2/44–2002/4495; A61F 2/4611
    See application file for complete search history.

(56) References Cited

U.S. PATENT DOCUMENTS 2,999,769 A * 9/1961 Korpman ................. C09J 7/045
                                                    427/208.4
4,689,832 A * 9/1987 Mulvaney .............. A41D 19/00
                                                       2/161.1
(Continued)

FOREIGN PATENT DOCUMENTS

DE     EP 1078966 A1 *  2/2001  ............ C09J 7/0214
JP        2001-508320 A    6/2001
(Continued)

OTHER PUBLICATIONS

International Search Report (PCT/ISA/210) dated Jun. 4, 2013, by the Japanese Patent Office as the International Searching Authority for International Application No. PCT/JP2013/060025.

*Primary Examiner* — Zade Coley

(74) *Attorney, Agent, or Firm* — Buchanan Ingersoll & Rooney PC

(57) ABSTRACT

An implant assembly smoothly causes a folded implant to indwell a living body, and which can smoothly expand the implant without causing the implant to be displaced from a predetermined indwelling position when a filling material is injected. The implant assembly has the implant that is configured to be transformable from a folded and contracted state to an expanded state by the introduced filling material, and in which at least a portion of a surface thereof is covered with a covering material m whose friction coefficient increases by coming into contact with a body fluid, and guiding means for preventing the implant and the body fluid of the living body from coming into contact with each other inside the living body, and for guiding the implant to move to the indwelling position inside the living body.

19 Claims, 12 Drawing Sheets

(51) Int. Cl.
*A61B 17/70* (2006.01)
*A61F 2/30* (2006.01)

(52) U.S. Cl.
CPC .......... *A61F 2/4405* (2013.01); *A61F 2/4611* (2013.01); *A61F 2002/3013* (2013.01); *A61F 2002/30583* (2013.01); *A61F 2002/4623* (2013.01)

(56) References Cited

U.S. PATENT DOCUMENTS

| | | | | |
|---|---|---|---|---|
| 5,117,509 | A | * | 6/1992 | Bowers ............ A41D 19/01547 2/161.1 |
| 5,496,292 | A | * | 3/1996 | Burnham .......... A61M 25/0012 600/434 |
| 5,647,846 | A | * | 7/1997 | Berg ................ A61M 25/0012 604/264 |
| 5,746,745 | A | * | 5/1998 | Abele .................... A61F 2/958 604/103.08 |
| 5,792,172 | A | * | 8/1998 | Fischell .................. A61F 2/958 606/194 |
| 5,913,871 | A | * | 6/1999 | Werneth .................. A61F 2/958 606/195 |
| 6,033,380 | A | * | 3/2000 | Butaric ............ A61M 25/1002 604/103.07 |
| 6,441,092 | B1 | * | 8/2002 | Gieselman ............. A61L 15/58 156/327 |
| 6,458,867 | B1 | | 10/2002 | Wang et al. |
| 2003/0130717 | A1 | * | 7/2003 | Hale ....................... A61F 2/958 623/1.11 |
| 2003/0139800 | A1 | * | 7/2003 | Campbell ................. A61F 2/86 623/1.15 |
| 2003/0195628 | A1 | | 10/2003 | Bao et al. |
| 2005/0256366 | A1 | * | 11/2005 | Chu ................. A61B 17/06066 600/30 |
| 2006/0234047 | A1 | * | 10/2006 | Wenninger ............. C09J 7/0214 428/355 R |
| 2007/0167973 | A1 | * | 7/2007 | Stupecky .............. A61M 25/10 606/192 |
| 2009/0118833 | A1 | * | 5/2009 | Hudgins ........... A61B 17/7065 623/17.16 |
| 2009/0139010 | A1 | * | 6/2009 | Bevier ................. A63B 71/148 2/161.8 |
| 2010/0262240 | A1 | | 10/2010 | Chavatte et al. |
| 2012/0209329 | A1 | * | 8/2012 | Hata .................. A61B 17/8816 606/249 |

FOREIGN PATENT DOCUMENTS

| | | |
|---|---|---|
| JP | 2003-510134 A | 3/2003 |
| JP | 2004-507319 A | 3/2004 |
| JP | 2005-514178 A | 5/2005 |
| JP | 2011-502711 A | 1/2011 |
| WO | WO 97/31674 A1 | 9/1997 |
| WO | WO 01/23015 A1 | 4/2001 |
| WO | WO 02/17825 A2 | 3/2002 |
| WO | WO 03/059430 A1 | 7/2003 |
| WO | WO 2009/064847 A2 | 5/2009 |

* cited by examiner

IMPLANT ASSEMBLY

CROSS-REFERENCE TO RELATED APPLICATION

This application is a continuation of International Application No. PCT/JP2013/060025 filed on Apr. 2, 2013, the entire content of which is incorporated herein by reference.

TECHNICAL FIELD

The disclosure herein relates to an implant assembly including an implant which is caused to be indwelled in a living body.

BACKGROUND DISCUSSION

In a medical field, techniques relating to an implant which is caused to be indwelled in a living body or various techniques relating to a method for causing the implant to indwell in the living body are known.

For example, U.S. Patent Application Publication No. 2009/0118833 discloses an implant which is expanded by the introduction of a filling material. The implant in a folded state is percutaneously inserted into the living body, and is caused to indwell in the living body. The implant which indwells in the living body gradually expands after an end portion on a filling material injected side (proximal portion side) is first filled with the filling material. At this time, if the filling material is injected into the implant in a state where a structure in a body comes into contact with or interferes with an outer surface of the implant, the filling material inside the implant does not evenly spread. Consequently, in some cases, the implant unevenly expands. If the filling material is continuously injected to the unevenly expanding implant, injecting pressure applies pressing force to a portion which comes into contact with or interferes with the structure in the body. In some cases, reaction of the pressing force causes the implant to be displaced from an indwelling position of the implant. For this reason, when the filling material is injected into the implant which is indwelled at a determined position, it is necessary to provide a method of preventing the implant from being displaced from the indwelling position.

In contrast, JP-T-2001-508320 discloses a balloon catheter in which a surface of the folded balloon catheter is initially covered with a high-strength adhesive material so as to prevent a balloon from being displaced when the balloon dilates.

It is considered possible to prevent the implant from being displaced from the indwelling position if the implant employs the technique of initially covering the surface with the high-strength adhesive material.

However, when the surface of the folded implant is initially covered with the high-strength adhesive material, the adhesive material disadvantageously sticks thereto. Consequently, even if the filling material is injected into the implant, the implant becomes less likely to expand. In addition, if the surface of the implant is initially covered with the high-strength adhesive material, the implant cannot be smoothly introduced into the living body.

SUMMARY

The disclosure herein provides an implant assembly in which a folded implant can be smoothly introduced into a living body, and in which the implant can smoothly expand without causing the implant to be displaced from an indwelling position when a filling material is injected.

An implant assembly includes an implant that is configured to be transformable from a folded and contracted state to an expanded state by an introduced filling material, and in which at least a portion of a surface thereof is covered with a covering material whose friction coefficient increases by coming into contact with a body fluid, and guiding means for preventing the implant and the body fluid of a living body from coming into contact with each other inside the living body, and for guiding the implant to move to an indwelling position inside the living body.

In the implant, a first surface portion which is exposed outward and a second surface portion which is covered with the first surface portion so as to be positioned on an inner side of the first surface portion are formed on a surface of the implant in the folded and contracted state, and the covering material covers only the second surface portion.

Further, the implant has a body section which extends in a longitudinal direction, and a wide section which is disposed in both ends of the body section and whose width in a direction intersecting the longitudinal direction is greater than the width of the body section in a state after the implant expands, and the covering material is disposed in only the wide section.

In addition, the guiding means has a lumen into which the implant can be inserted, and friction reducing means for reducing friction between the lumen and the implant disposed in at least a portion on an inner surface of the guiding means which is formed by the lumen.

Further still, the friction reducing means is configured so that the inner surface of the guiding means is formed in an uneven shape.

An absorber which can absorb the body fluid can also be disposed inside a recessed groove formed on the inner surface of the guiding means.

The friction reducing means is configured to include a low friction member which covers the inner surface of the guiding means.

In the above-described implant assembly, the implant is used in order to expand a site between bones, a site between cartilages, a site inside the cartilage, or a site inside the bone in the living body.

According to an exemplary embodiment of the disclosure, the implant assembly includes the implant and the guiding means. At least a portion of the surface of the implant is covered with the covering material whose friction coefficient increases by coming into contact with the body fluid. Therefore, the covering material on the surface of the implant and the body fluid come into contact with each other inside the living body, thereby increasing the friction coefficient. Accordingly, when the filling material is injected, the implant can be smoothly expanded without being displaced from a predetermined indwelling position. The guiding means prevents the implant and the body fluid of the living body from coming into contact with each other inside the living body, and guides the implant to move to the indwelling position inside the living body. Therefore, it is possible to prevent an increase in the friction coefficient of the covering material on the surface of the implant while the implant moves to the indwelling position. This enables the implant to be smoothly introduced into the living body.

According to another aspect of the disclosure, the surface of the implant in the folded and contracted state is configured so that only the second surface portion, which is covered with the first surface portion exposed outward so as to be positioned on the inner side of the first surface portion, is covered with the covering material. Accordingly, when the body fluid is likely to permeate into the guiding means while the implant moves to the indwelling position, it is possible to preferably prevent the covering material and the body fluid from coming into contact with each other. Therefore, it is possible to prevent an increase in the friction coefficient of the covering material on the surface of the implant while the implant moves to the indwelling position. This enables the implant to be smoothly introduced into the living body.

According to a further aspect of the disclosure, the implant has the body section which extends in the longitudinal direction, and the wide section which is disposed in both ends of the body section and whose width in the direction intersecting the longitudinal direction is greater than the width of the body section in the state after the implant expands. Since the implant has this shape, the covering material is disposed in at least the wide section in which a variation amount thereof is largest and an area in contact with the living body is largest before and after the implant is expanded and transformed. Therefore, it is possible to prevent the implant from being displaced from the predetermined indwelling position when the filling material is injected.

In a still further aspect of the disclosure, the friction reducing means is disposed on the inner surface of the guiding means. Accordingly, the friction between the implant and the guiding means is reduced. In this manner, the implant can be smoothly introduced into the living body.

According to another aspect of the disclosure, the inner surface of the guiding means is formed in an uneven shape such as a recessed groove. Accordingly, the contact area between the implant and the guiding means decreases. Therefore, the implant can be smoothly introduced into the living body. In addition, even when the body fluid is likely to permeate into the inner surface of the guiding means, the body fluid can be evacuated into the recessed groove. Accordingly, it is possible to prevent the covering material on the surface of the implant and the body fluid from coming into contact with each other, when the implant moves to the indwelling position inside the living body. Therefore, it is possible to prevent an increase in the friction coefficient of the covering material on the surface of the implant while the implant moves to the indwelling position. In this manner, the implant can be smoothly introduced into the living body.

According to a further aspect of the disclosure, the absorber which can absorb the body fluid is disposed inside the recessed groove formed on the inner surface of the guiding means. Thus, the body fluid evacuated into the groove can be held. Accordingly, it is possible to more reliably prevent the covering material on the surface of the implant and the body fluid from coming into contact with each other, when the implant moves to the indwelling position inside the living body. Therefore, it is possible to more reliably prevent an increase in the friction coefficient of the covering material on the surface of the implant while the implant moves to the indwelling position. This enables the implant to be smoothly introduced into the living body.

According to a further aspect of the disclosure, the friction reducing means is configured to include the low friction member which covers the inner surface of the guiding means. Accordingly, the friction between the implant and the guiding means is more reliably reduced. Therefore, it is possible to prevent an increase in the friction coefficient of the covering material on the surface of the implant while the implant moves to the indwelling position. This enables the implant to be smoothly introduced into the living body.

According to the disclosure herein, it is thus possible to provide an implant assembly which is easily introduced into the living body without any positional displacement such that it can be indwelled at a site between bones, a site between cartilages, a site inside the cartilage, or a site inside the bone in the living body.

DETAILED DESCRIPTION

Figure 1:
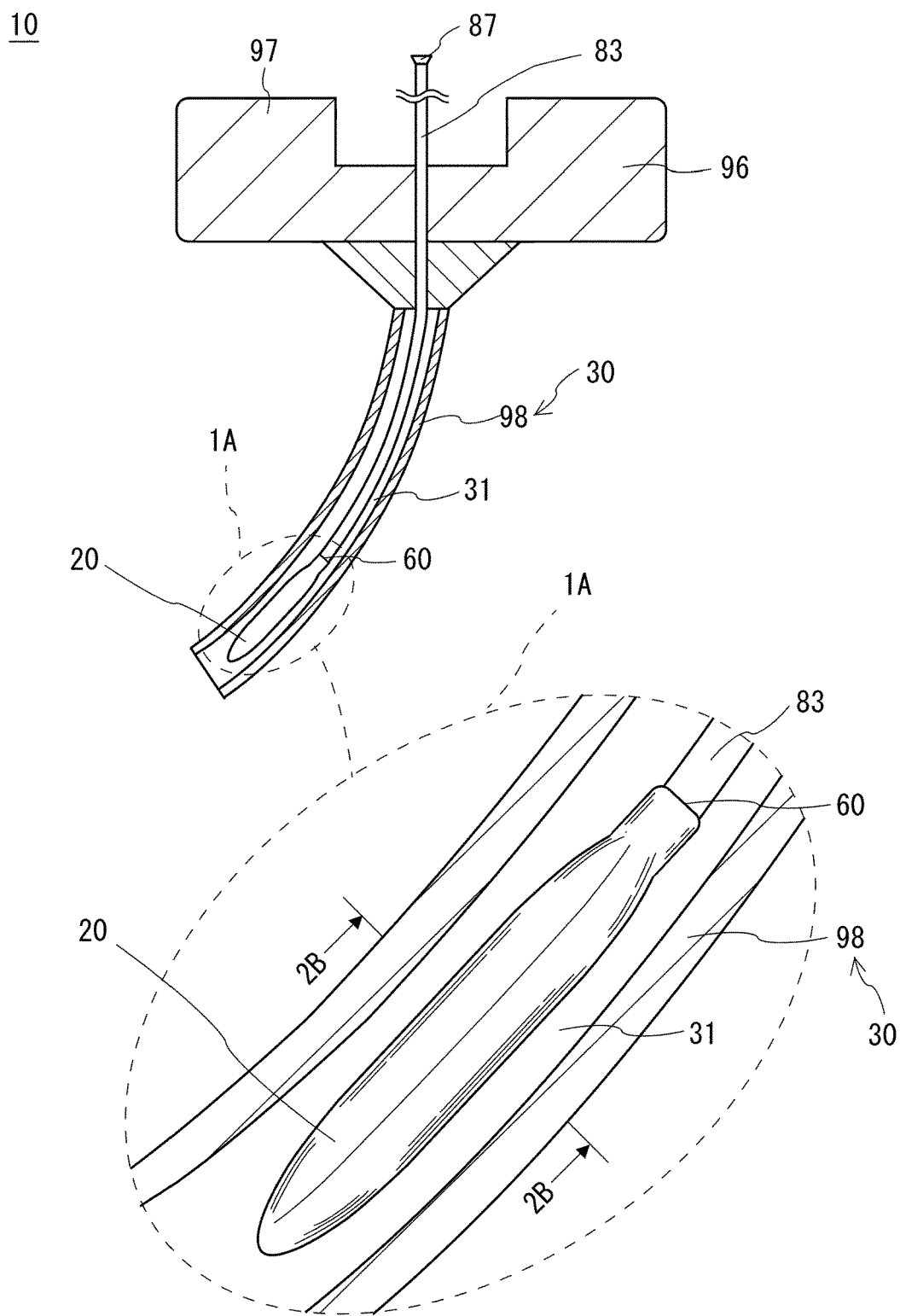
FIG. 1 is a schematic view for describing an implant assembly according to a first exemplary embodiment of the disclosure.

Hereinafter, the disclosure herein will be described with reference to exemplary embodiments and the drawings. In the description of the drawings, the same reference numerals are given to the same elements, and repeated description thereof will be omitted. Dimensional ratios in the drawings are exaggerated in order to facilitate the description, and may be different from actual ratios in some cases.

In the exemplary embodiments, an example will be described in which the disclosure is applied to a medical device used in order to introduce an implant into a site between spinous processes adjacent to each other inside a living body. First, referring to FIGS. 5A, 5B, and 5C, the spinous process or a treatment target disease in the living body which an implant 20 is caused to indwell will be briefly described.

Figure 5A:
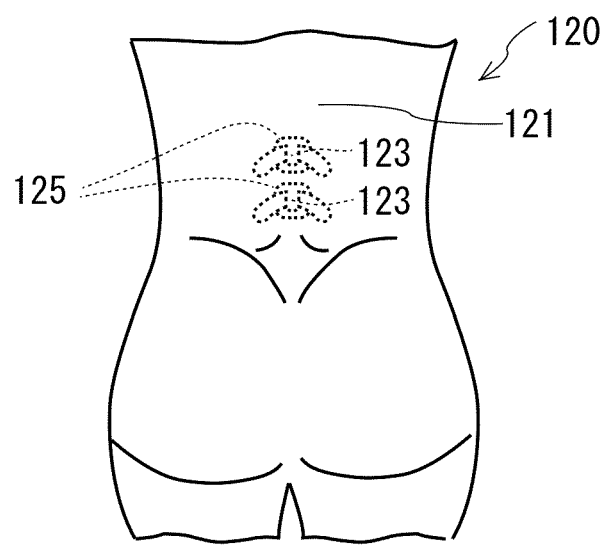
FIG. 5A is a view for describing a spinous process of the living body to which the implant is applied, and is a view briefly illustrating a lumbar region of the living body.
Figure 5B:
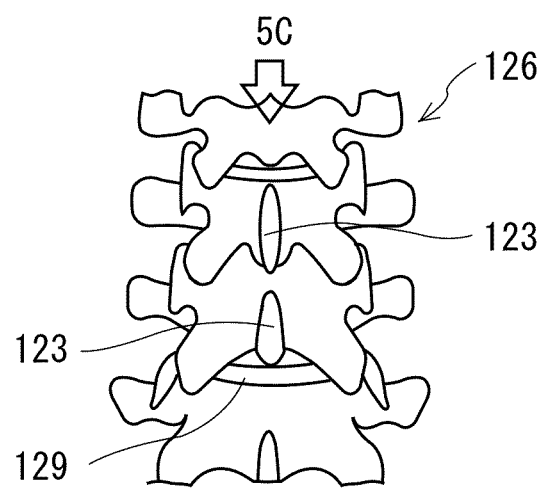
FIG. 5B is a view for describing the spinous process of the living body to which the implant is applied, and is an enlarged view of a lumbar vertebra.
Figure 5C:
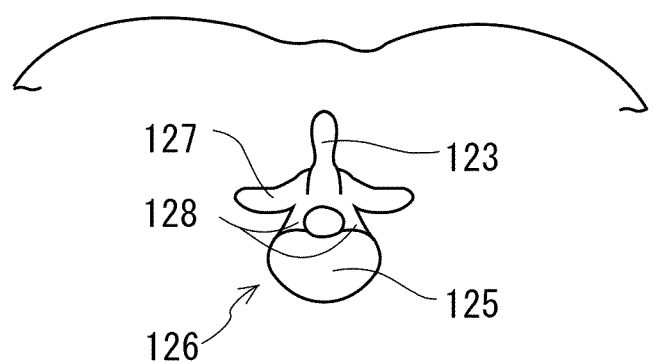
FIG. 5C is a view for describing the spinous process of the living body to which the implant is applied, and is a sectional view of the lumbar vertebra when viewed in a direction of an arrow 5C in FIG. 5B.

FIG. 5A is a view schematically illustrating a state where the spinous process is perspectively viewed from the back side of the living body. FIG. 5B is an enlarged view of a peripheral portion of the spinous process illustrated in FIG. 5A. FIG. 5C is a view schematically illustrating a cross section (horizontal cross section) of the living body in a direction orthogonal to an arrayed direction of the spinous processes (extending direction of the spine). In each drawing, the X-axis indicates the direction orthogonal to the arrayed direction of the spinous processes, the Y-axis indicates the arrayed direction of the spinous processes, and the Z-axis indicates a thickness direction of the living body.

Multiple lumbar vertebrae 126 are arrayed along the extension direction of the spine in a back 121 of a living body 120 (refer to FIG. 5B). The lumbar vertebrae 126 have a configuration in which a vertebral body 125 in the front half and a lamina of vertebral arch 127 in the rear half are connected to each other via a pedicle of vertebral arch 128 (refer to FIGS. 5B and 5C). Various processes such as a spinous process 123, a transverse process (costal process), a superior articular process, an inferior articulate process, and the like are formed in the lamina of vertebral arch 127. The lumbar vertebra 126 normally has a shape which is curved slightly forward from the living body 120. In addition, the vertebral bodies 125 adjacent to each other are connected via an intervertebral disk (disk between vertebrae) 129. A certain vertebral body and a vertebral body adjacent to the certain vertebral body are not displaced from each other, since the intervertebral disk 129 are provided, and an intervertebral joint or the like which is present between the superior articular process and the inferior articulate process (refer to FIG. 5B).

For example, in a case where a stress fracture or the like occurs due to repeated loads applied to the lumbar vertebra 126 by sports and the like, spondylolysis develops in which the vertebral body 125 and the lamina of vertebral arch 127 are separated from each other in a portion of the pedicle of vertebral arch 128. In some cases, due to the deformed intervertebral joint or the degenerated intervertebral disk 129, the lumbar vertebra 126 positioned on the upper side is less likely to be fixed, thereby causing spondylolisthesis in which the vertebral bodies are displaced from each other. Due to the spondylolysis, the spondylolisthesis, and a disease in which a ligament arranged around the lumbar vertebra is degenerated with advancing years, a spinal canal is stenosed, thereby causing intermittent claudication which is a symptom of lumbar spinal canal stenosis in some cases.

Figure 8A:
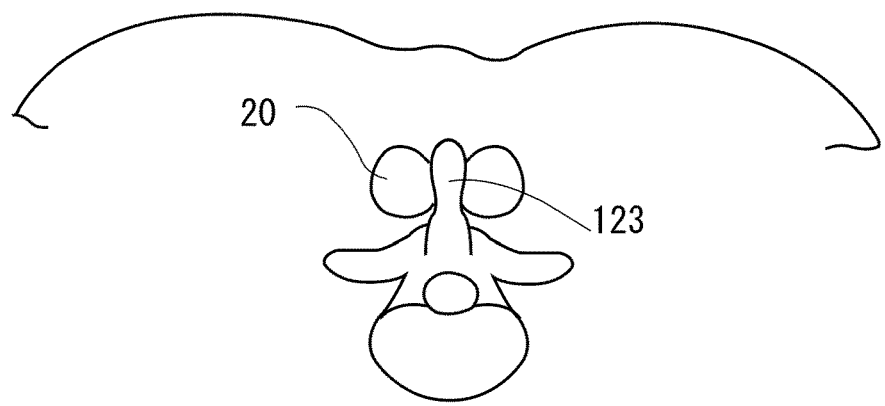
FIG. 8A is a view illustrating the implant indwelled in the spinous processes, and is a sectional view illustrating the spinous processes and the implant.
Figure 8B:
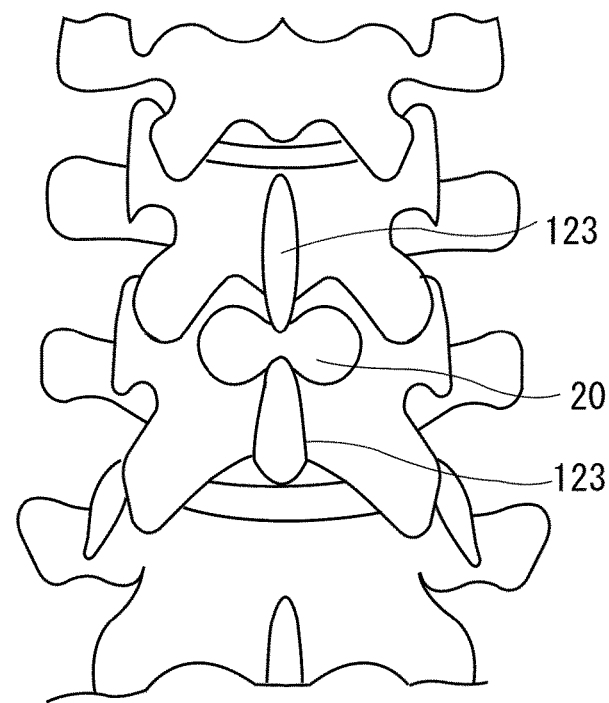
FIG. 8B is a view illustrating the implant indwelled in the spinous processes, and is a rear view illustrating the spinous processes and the implant.

As a treatment method for this lumbar spinal canal stenosis, a treatment method is provided in which the implant 20 which can function as a spacer is caused to indwell between the mutually adjacent spinous processes 123 so as to suppress the spinal canal stenosis (refer to FIGS. 8A and 8B). According to the first exemplary embodiment, the implant assembly 10 is used for causing the implant 20 to be indwelled in the living body.

Next, a configuration of the implant assembly 10 according to the present embodiment will be described.

Figure 3A:
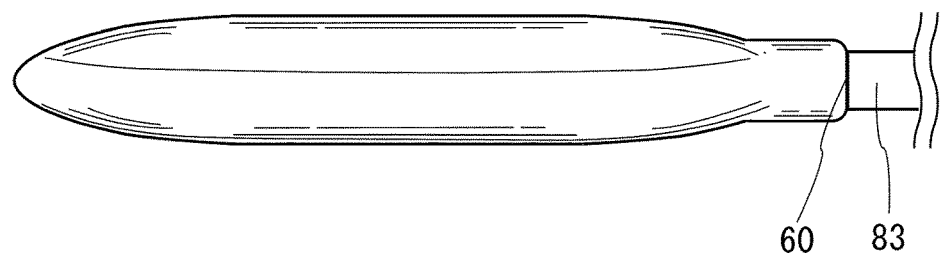
FIG. 3A is a schematic view for describing the implant assembly according to the first exemplary embodiment of the disclosure before the implant assembly is expanded and transformed.
Figure 3B:
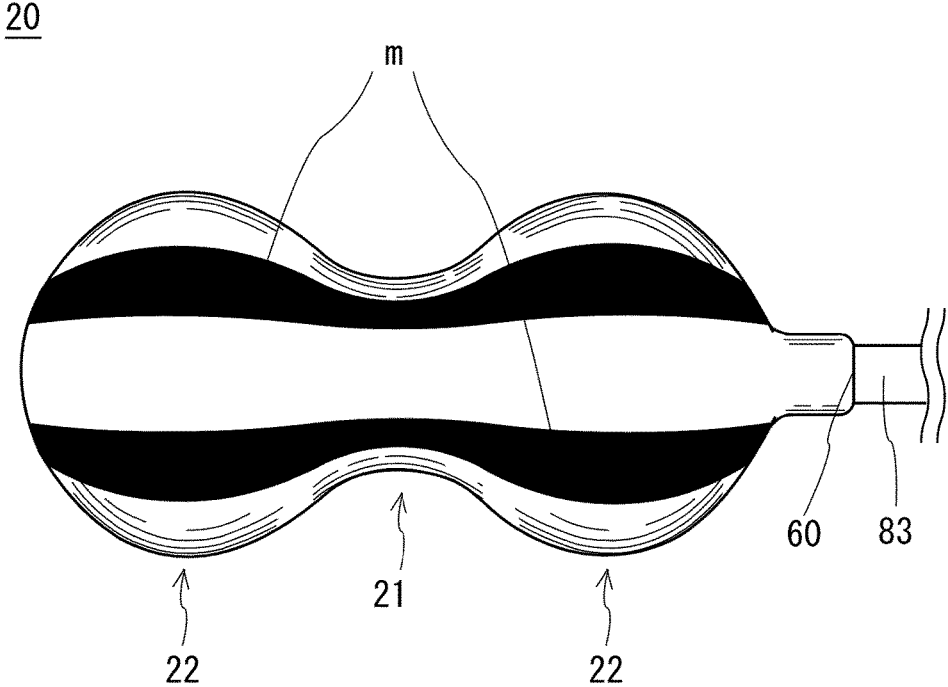
FIG. 3B is a schematic view for describing the implant assembly according to the first exemplary embodiment of the disclosure after the implant assembly is expanded and transformed.

In brief, as illustrated in FIGS. 1, 3A, and 3B, the implant assembly 10 according to the first embodiment of the disclosure includes the implant 20 that is configured to be transformable from a folded and contracted state to an expanded state by the introduced filling material, and in which at least a portion of a surface thereof is covered with a covering material m whose friction coefficient increases by coming into contact with a body fluid, and guiding means 30 for preventing the implant 20 and the body fluid of the living body from coming into contact with each other inside the living body, and for guiding the implant 20 to move to the indwelling position inside the living body. As described above, the implant assembly 10 is configured to include the implant 20 and the guiding means 30.

Figure 7A:
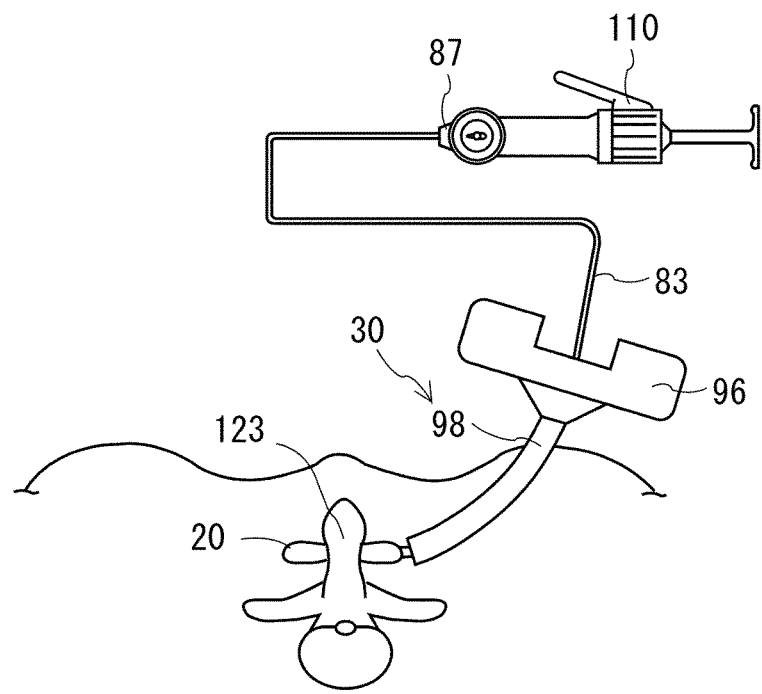
FIG. 7A is a view for describing the implant being indwelled in the living body, and is a view illustrating a state where the implant is positioned between the spinous processes.

The implant 20 in a folded and contracted state is introduced into the living body 120 (refer to FIG. 7A). In addition, after being positioned at an indwelling position in the vicinity of the spinous process 123, the implant 20 is expanded and transformed by the injected filling material thereinside. The implant 20 in an expanded and transformed state indwells in the living body 120 (refer to FIG. 7B). At this time, the covering material m on the surface of the implant 20 and the body fluid come into contact with each other inside the living body 120, thereby increasing the frictional coefficient. Accordingly, it is possible to smoothly expand the implant 20 without causing the implant 20 to be displaced from a predetermined indwelling position when the filling material is injected. In this way, the implant 20 is used in order to expand a site between bones, a site between cartilages, a site inside the cartilage, or a site inside the bone in the living body.

A body section 21 which extends in a longitudinal direction and a wide section 22 provided with a lager width than that of the body section 21 are formed in the expanded and transformed implant 20. The body section 21 is formed in the central part of the implant 20, and the wide sections 22 are respectively formed in both end portions of the implant 20 so as to interpose the body section 21 therebetween. An outer shape of the expanded and transformed implant 20 is a dumbbell shape (substantially H-shape). In the body section 21 of the implant 20, a distance is held between the spinous processes 123 adjacent to each other. In addition, the wide sections 22 respectively positioned in both end portions of the implant 20 interpose the spinous process 123 therebetween. In this manner, the implant 20 is prevented from being displaced after the implant 20 is indwelled. The shape of the expanded and transformed implant 20 can be appropriately changed as long as the expanded and transformed implant can function as a spacer which supports bones inside the living body or holds the distance between the bones. In the exemplary embodiment, a case has been described where the outer shape of the expanded and transformed implant 20 is the dumbbell shape (substantially H-shape). However, the exemplary embodiment may employ a straight shape which is a constant width having no wide section, for example. Alternatively, the exemplary embodiment may employ an hourglass shape which is a shape whose width gradually increases from the central portion toward the end portion.

In the exemplary embodiment, a configuration is described in which at least a portion of the surface of the implant 20 is covered with the covering material m. A specific covering position of the covering material m will be described in detail as follows.

Figure 2:
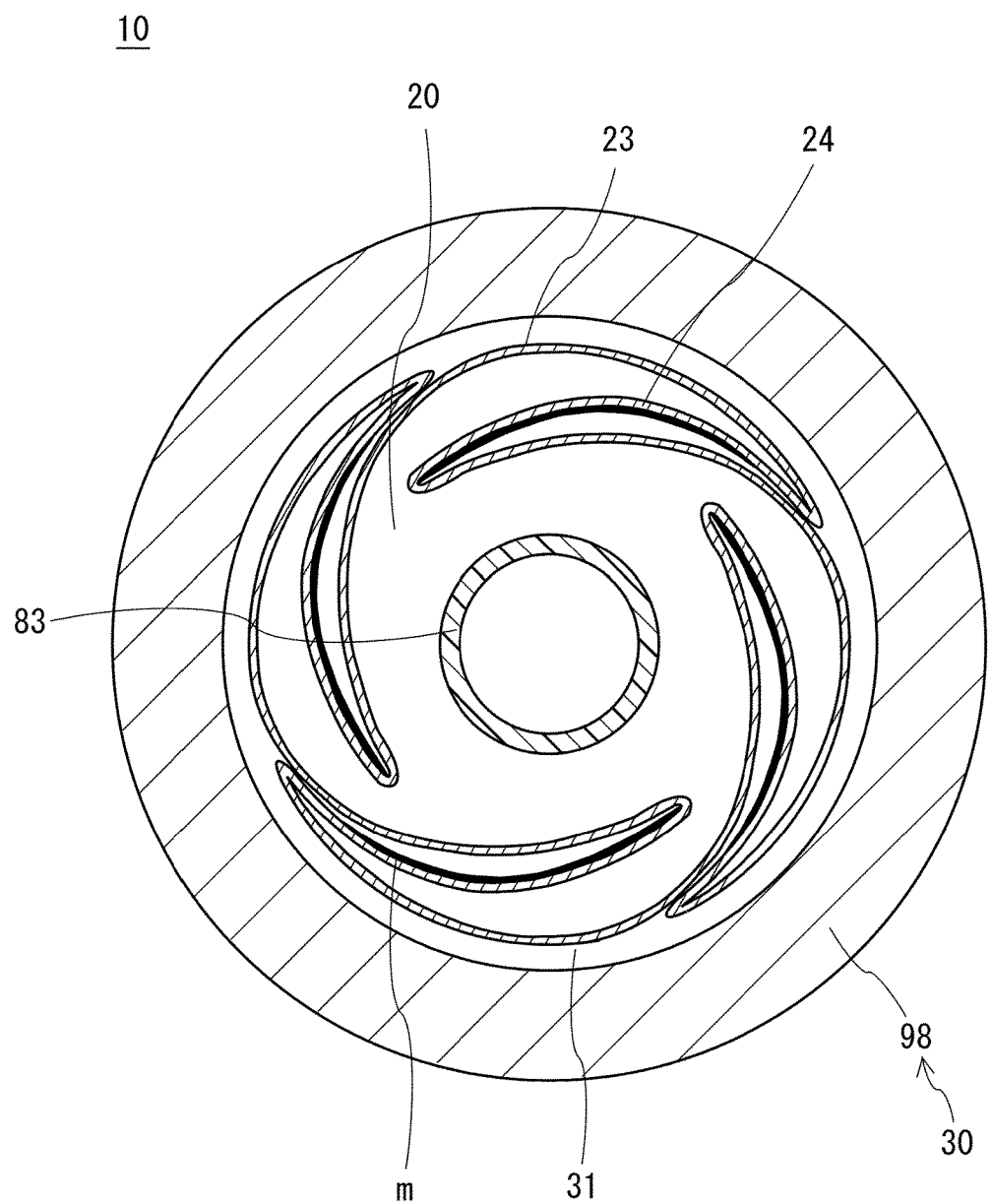
FIG. 2 is a sectional view taken along line 2B-2B in FIG. 1.

As illustrated in FIG. 2, a first surface portion 23 which is exposed outward and a second surface portion 24 which is covered with the first surface portion 23 and is positioned on the inner side of the first surface portion 23 are formed on the surface of the implant 20 in a folded and contracted state. The covering material m covers only the second surface portion 24.

In the implant 20 in the folded and contracted state, the covering material m covers only the second surface portion 24 which is covered with the first surface portion 23 exposed outward and which is positioned on the inner side of the first surface portion 23. Therefore, even if the body fluid permeates the guiding means 30 while the implant 20 is moved to the indwelling position by the guiding means 30, since the covering material m covers only the second surface portion 24 which is covered with the first surface portion 23, the covering material m does not come into contact with the body fluid. Therefore, the covering material m does not hinder the implant 20 from being introduced into the living body, and thus the implant 20 can be smoothly introduced into the living body.

If the implant 20 is filled with the filling material, the covering material m which covers only the second surface portion 24 of the implant 20 in the folded state is exposed on the surface of the implant 20 as illustrated in FIG. 3B. The covering material m which is exposed on the surface of the implant 20 comes into contact with the body fluid, thereby increasing the friction coefficient.

As a base material of the implant 20, any material can be selectively used among known plastic base materials such as a polyester resin base material, a polyamide resin base material, a polyolefin resin base material, polyimide resin base material, an ethylene vinyl alcohol copolymer base material, a polyvinyl chloride resin base material, and the like, or a combination of these base materials, or alternatively known base materials or the like in which the above-described materials are subjected to matting treatment, corona discharge treatment, plasma treatment, ultraviolet radiation treatment, electron beam radiation treatment, flame plasma treatment, and ozone treatment, or surface treatment such as various types of easy adhesion treatment and the like.

The implant 20 can be expanded by filling the inside of the implant 20 with various filling materials such as a solid, a fluid (gas, liquid, gel), and the like. A material for the filling materials is not particularly limited. However, in order to maintain the expanded state for a long time, the filling material preferably employs the solid material or a curing material which is fluidic when being introduced into the implant 20 and is cured after being introduced (hereinafter, simply referred to as a "curing material").

For example, the material of the covering material m employs natural products, chemically modified natural products, synthetic products, or mixtures of two or more types of these products. For example, as a specific example of the above-described materials, the synthetic products can include polyvinyl alcohol, polyvinyl methyl ether, polyvinyl pyrrolidone, polyacrylamide, polyethylene oxide, polyacrylic acid-containing polymer, polycarboxylic acid-containing polymer, cationic resin, poly-N-vinyl-2-pyrrolidone, styrene-maleic anhydride copolymer, ethylene-maleic anhydride copolymer, and the like. The natural products can include agar, starch, proteins, carrageenan, guar gum, gum arabic, tragacanth gum, locust bean gum, and the like. The chemically modified natural products can include cationic starch, dextran, hydroxyalkyl starch, methyl cellulose, sodium carboxymethyl cellulose, xanthan gum, dextrin, and the like.

In addition, the covering material m can contain a compatible liquid plasticizer, a filling material, or both of these. If the liquid plasticizer is contained, flexibility of a wetting adhesive is improved, and the body fluid, water, or a hydrophilic medium is satisfactorily absorbed. Accordingly, the covering material m is allowed to show quick adhesive performance. In addition, if the filling material is contained, it is possible to improve mechanical strength of the covering material.

The liquid plasticizer may employ alkylene glycol, polyalkylene glycol, glycerol, polyglycerol, and sorbitol, or alternatively may contain one, two or more types in combination among the above-described materials.

A method of forming the covering material m can be selectively chosen from known methods such as a method of dipping the implant 20 into a solution dissolved or dispersed in a solvent, a method of spraying a solution onto the surface of the implant 20, and the like. By way of example, the solvent employs an organic solvent such as alcohol, acetone, tetrahydrofuran, dimethyl sulfoxide, water, and hexane.

The filling material can employ one or more types of an organic filling material such as polymethyl methacrylate or the like, inorganic oxide or inorganic composite oxide such as silica, alumina, zinc oxide, titanium oxide, talc, clay, kaolin, glass, or the like, an inorganic filling material such as barium sulfate, calcium carbonate, calcium phosphate, hydroxyapatite, ceramics, carbon, or the like, and a metal filling material such as stainless steel, titanium, nickel-titanium alloy, or the like (wire shape, coil shape, or the like). After the filling material is introduced into the implant 20, an indwelling state of the implant 20 is maintained without being adversely affected by the movement of the body. Accordingly, the implant 20 can function as a spacer between the spinous processes 123 for a long period of time in a state where the implant 20 is expanded and transformed.

The curing material preferably has at least one of the following characteristics: (1) safe for a patient; (2) no or little damage to tissues; (3) curable at temperature close to a patient's body temperature (approximately 35° C. to 42° C.); (4) no contraction or no expansion, the cured shape can be maintained; (5) cured within 1 minute to 60 minutes, preferably 5 minutes to 30 minutes, more preferably within 10 minutes after injection; (6) as a solvent, water, a buffer solution, physiological saline, a contrast medium, or fats and oils such as olive oil, castor oil, and the like can be used.

In addition, a specific example of the curing material includes (a) two-liquid mixture cross-linked polymer; (b) hot melt adhesive; (c) urethane elastomer; (d) a light-curable resin; (e) an acrylic resin; (f) bone cement; (g) a solution or the like which is crystallized by external stimulus.

In the above-described (a), as the two-liquid mixture cross-linked polymer, it is preferable to combine an aromatic diepoxide resin or an aliphatic diepoxide resin and an amine compound, or alternatively to combine polyorganosiloxane having a reactive group, a crosslinking agent, and a curing catalyst.

In the above-described (b), the hot melt adhesive includes a combination of water and a material which can be cured through a reaction with water, an ethylene-vinyl acetate copolymer (EVA) system, a polyolefin (PO) system, a polyamide (PA) system, a synthetic rubber (SR) system, an acrylic (ACR) system, a polyurethane moisture-curing (PUR) system, or the like.

In the above-described (c), as the urethane elastomer, it is preferable to use a polymer derived from polyol and aromatic polyisocyanate.

In the above-described (d), the photopolymerizable monomer includes acrylic ester, methacrylic acid ester, ethylenically unsaturated carboxylic acid, or the like. If necessary, it is possible to use a polymerization accelerator, a crosslinking agent, a photoinitiator, or the like.

In the above-described (e), the acrylic resin includes those which are obtained by using a known method to polymerize monomers such as methyl (meth)acrylate, ethyl (meth)acrylate, butyl (meth)acrylate, n-hexyl (meth)acrylate, cyclohexyl (meth)acrylate, 2-ethylhexyl (meth)acrylate, n-octyl (meth)acrylate, nonyl (meth)acrylate, decyl (meth)acrylate, (meth)acrylate, glycidyl (meth)acrylate, vinyl acetate, styrene, α-methyl styrene, (meth) acrylamide, (meth)acrylonitrile, or the like.

In the above-described (f), for example, the bone cement is produced by mixing powder such as polymethyl methacrylate, methyl methacrylate-styrene copolymer, benzoyl peroxide, barium sulfate, or the like with a solvent containing methyl methacrylate, N,N-dimethyl-para-toluidine, hydroquinone, or the like. Alternatively, it is also possible to use an organic-inorganic composite material or the like in which organic sodium alginate and inorganic calcium phosphate are produced by mixing a solvent with dental cement cured by an acid-base reaction between zinc oxide and phosphoric acid, sodium alginate, phosphoric acid, calcium chloride, or the like.

In the above-described (g), the solution crystallized by external stimulus includes an aqueous solution obtained by dissolving sodium acetate, sodium chloride, or the like. The external stimulus includes physical shock, heat, light, electricity, ultrasound, or the like.

The curing material which is fluidic when being introduced and is cured after being introduced is used as the filling material. Accordingly, similarly to a case where the filling material employs the solid, the implant 20 can function as a spacer between the spinous processes 123 for a long time in a state where the implant 20 is expanded and transformed.

One introduction port 60 is disposed in the implant 20. The introduction port 60 is disposed in a proximal side portion in the direction in which the implant 20 is introduced into the living body. The inside of the implant 20 can be filled with the filling material by using the introduction port 60.

A tubular member 83 used in feeding the filling material to the inside of the implant 20 via the introduction port 60 has a configuration in which the tubular member 83 is attachable to and detachable from the introduction port 60. According to this configuration, the tubular member 83 is attachable to and detachable from the implant 20. In addition, the introduction port 60 has a sealing portion (not illustrated). This sealing portion can maintain liquid-tight and air-tight states between the implant 20 and the tubular member 83. Alternatively, the introduction port 60 includes a joint having a detachable Luer-lock shape, a joint of male and female screws which can be detached by twisting a pumping tube itself, or the like.

The implant 20 and the tubular member 83 are separated from each other by pulling a distal end of the tubular member 83 which is inserted into the implant 20 out from the inside of the implant 20. If the distal end of the tubular member 83 is pulled out, the sealing portion is elastically deformed, thereby closing the introduction port 60.

The tubular member 83 is configured to include a tube which has a lumen (not illustrated) formed thereinside. For example, the tube can be configured to include a known resin-made tube or the like which is widely used in a medical field or the like.

A connector 87, to which a filling material supply unit 110 (refer to FIGS. 7A and 7B) for feeding the filling material is connected, is disposed on the proximal side of the tubular member 83 (refer to FIG. 7A). The connector 87 functions as a valve for maintaining liquid-tight and air-tight states inside the lumen of the tubular member 83.

For example, materials for configuring the tubular member 83 and the connector 87 may include fluorine resins which are excellent in biocompatibility, such as tetrafluoro 4 ethylene-ethylene copolymer (ETFE), polytetrafluoroethylene (PTFE), or the like, polyolefin such as polyethylene (PE), polypropylene (PP), or the like, and thermoplastic resins such as polyamide, polyester, polyurethane, or the like.

The guiding means 30 has a preventing function of preventing the implant 20 from coming into contact with the body fluid inside the living body as described above, and a guiding function of guiding the implant 20 to move to the indwelling position inside the living body.

The guiding means 30 in the illustrated embodiment includes a cylindrical portion 98. The cylindrical portion 98 also serves as a cylindrical portion which is disposed in an outer cylinder 96 in order to insert and remove a main body 92 of an inner needle 91, in a puncture device 90 (to be described later) used in introducing the implant 20 into the living body (refer to FIGS. 4A, 4B and 4C).

After the puncture device 90 punctures the living body, the folded implant 20 is introduced into the cylindrical portion 98 of the outer cylinder 96, and the cylindrical portion 98 guides the implant 20 to move to the indwelling position inside the living body. The cylindrical portion 98 belonging to the guiding means 30 also serves as a cylindrical portion of the outer cylinder 96 of the puncture device 90. Thus, the puncture device 90 will be first described in detail.

Figures 4A, 4B, 4C:
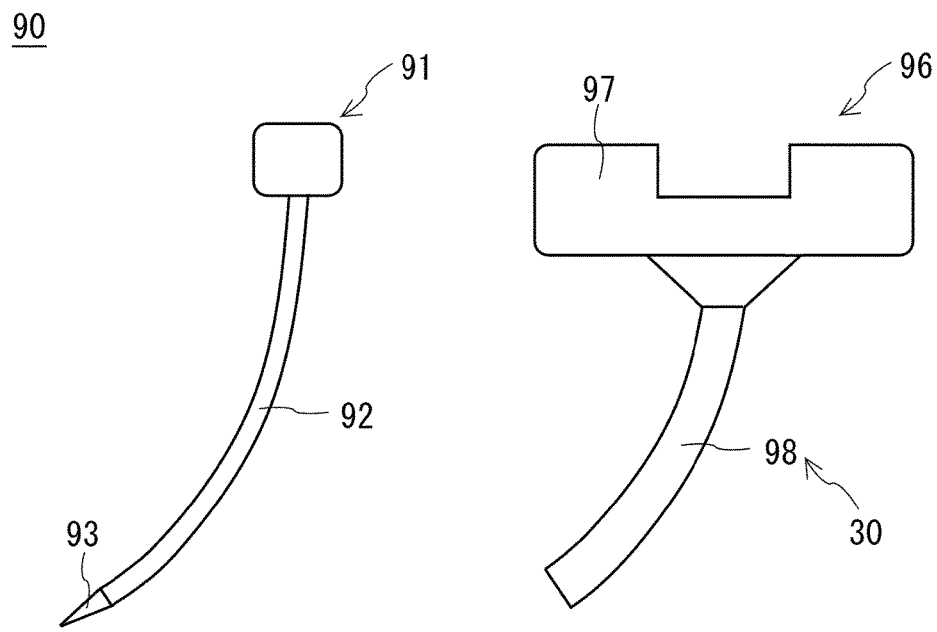
FIG. 4A is a view of a puncture device used to introduce the implant into the living body illustrating a state where the inner needle and the outer cylinder are assembled to and integrated with each other.
FIG. 4B is a view illustrating an inner needle of the puncture device shown in FIG. 4A.
FIG. 4C is a view illustrating an outer cylinder of the puncture device shown in FIG. 4A.

FIGS. 4A, 4C illustrate the puncture device 90 used in introducing the implant 20 into the living body. The puncture device 90 includes the inner needle 91 which punctures the living body and the outer cylinder 96 which is assembled with the inner needle 91. The inner needle 91 has the main body 92 whose distal end has a needle portion 93 disposed therein. The outer cylinder 96 has a grasping unit 97 and the cylindrical portion 98 which the main body 92 of the inner needle 91 can be inserted into and removed from.

In a state where the main body 92 of the inner needle 91 is inserted into the cylindrical portion 98 of the outer cylinder 96, the inner needle 91 and the outer cylinder 96 are fixed to each other (refer to FIG. 4A). Both of these are screwed and fixed by screw portions (not illustrated) formed in the main body 92 of the inner needle 91 and the cylindrical portion 98 of the outer cylinder 96. When the implant 20 is introduced, the inner needle 91 and the outer cylinder 96 are brought into an assembled state, and the needle portion 93 of the inner needle 91 punctures the living body 120 (refer to FIG. 6B). In this state, the inner needle 91 is separated from the outer cylinder 96, the main body 92 of the inner needle 91 is removed from the cylindrical portion 98, and the inner needle 91 is removed from the living body 120 as it is.

Next, the above-described preventing function and guiding function of the guiding means 30 will be described in detail.

The implant 20 is introduced into a predetermined site in the living body 120 by using the cylindrical portion 98 of the guiding means 30 which also serves as the cylindrical portion of the outer cylinder 96. At this time, the body fluid hardly permeates the implant 20 through an open distal end of the guiding means 30. The reason that the body fluid hardly permeates the implant 20 through the open distal end in this way is that the above-described puncture device 90 punctures a space between bones, a space between cartilage, an inside of the cartilage, or an inside of the bone in the living body. Accordingly, the permeating body fluid is mainly a lymph fluid or a tissue fluid rather than the blood. Compared to the blood, the lymph fluid or the tissue fluid has lower pressure and slower flow velocity of the liquid.

As described above, in the guiding means 30 configured to include the cylindrical portion 98, the body fluid hardly permeates the implant 20 through the open distal end. Accordingly, it is possible to prevent the implant 20 and the body fluid of the living body from coming into contact with each other inside the living body, and it is possible to guide the implant 20 to move to the indwelling position inside the living body. Therefore, it is possible to prevent an increase in the friction coefficient of the covering material m on the surface of the implant 20 when the implant 20 moves to the indwelling position. In this manner, the implant 20 can be smoothly introduced into the living body.

For example, materials for configuring the guiding means 30 include synthetic resins such as polycarbonate, polyolefin (for example, polyethylene, polypropylene, ethylene-propylene copolymer), styrene-based resin [for example, polystyrene, MS resin (methacrylate-styrene copolymer), MBS resin (methacrylate-butylene-styrene copolymer)], polyester, or the like, metal such as stainless steel, aluminum, an aluminum alloy, or the like, and the like.

An outer shape of the inner needle 91 is not particularly limited as long as the inner needle 91 can puncture the living body. For example, the inner needle 91 may have an outer shape which linearly extends. However, in this case, the cylindrical portion 98 of the outer cylinder 96 into which the inner needle is inserted is configured to have a shape for matching the outer shape of the inner needle 91.

Next, an indwelling procedure for providing the implant 20 and an operation of the implant 20 according to the exemplary embodiment will be described.

Figure 6A:
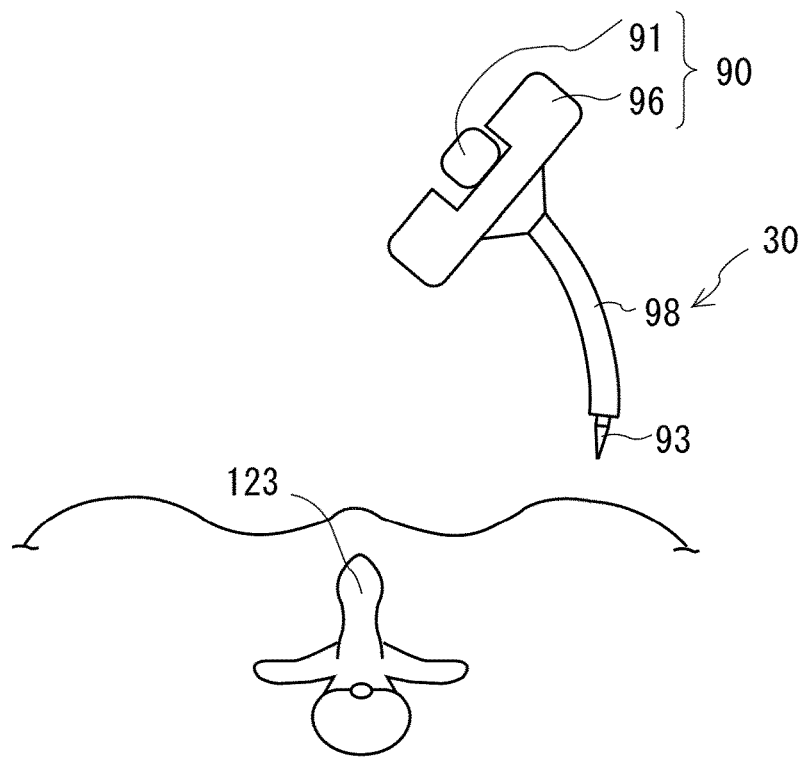
FIG. 6A is a view for describing the implant being indwelled in the living body, and is a view illustrating a state before the puncture device punctures the living body.

Referring to FIG. 6A, the puncture device 90 having the inner needle 91 and the outer cylinder 96 assembled therein is prepared.

Figure 6B:
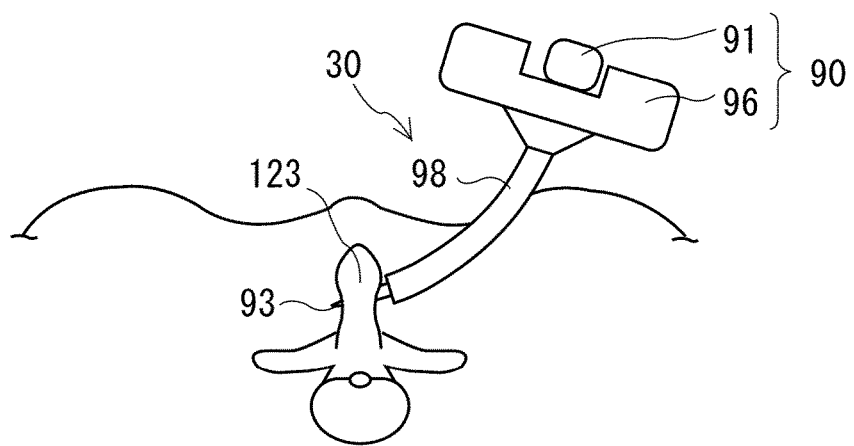
FIG. 6B is a view for describing the implant being indwelled in the living body, and is a view illustrating a state after the puncture device punctures the living body.

Referring to FIG. 6B, the puncture device 90 is introduced into the living body 120. At this time, the distal portion of the inner needle 91 and the distal portion of the outer cylinder 96 are positioned between spinous processes. Next, the inner needle 91 is separated and pulled out from the outer cylinder 96.

Referring to FIG. 7A, the implant 20 before being expanded and transformed is introduced into the living body 120 through the guiding means of the inner needle 91. The implant 20 extends out from the distal end of the outer cylinder 96, and is positioned between the spinous processes 123. A surgeon can press and introduce the implant 20 into the living body with his or her hand, or can press the implant 20 by using a pressing member such as a bar, a tube, or the like.

Figure 7B:
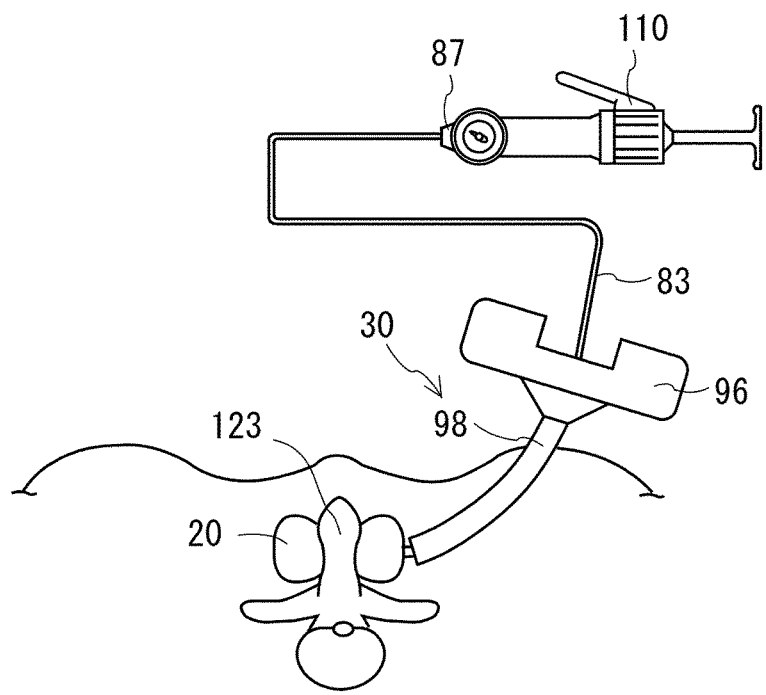
FIG. 7B is a view for describing the implant being indwelled in the living body, and is a view illustrating a state where the implant is expanded between the spinous processes.

Referring to FIG. 7B, the filling material is introduced into the implant 20, thereby expanding and transforming the implant 20.

When the filling material employs the curing material or the fluid, it is possible to use the filling material supply unit 110 for pumping the filling material. The filling material supply unit 110 can employ a known indeflator, a syringe, or the like. In addition, when the filling material supply unit 110 is used, the filling material supply unit 110 is connected via the connector 87 included in the tubular member 83. When the filling material employs the solid material, the filling material supply unit 110 is not used. The filling material can be introduced by causing the filling material to flow into or pressing the filling material into the guiding means 30 of the outer cylinder 96.

Before filling the implant 20 with the filling material, the inside of the implant 20 is filled with a contrast medium. The implant 20 preliminarily expands through this process. Accordingly, expanding can be smoothly carried out by using the filling material. In addition, X-ray fluoroscopy is performed in a state where the implant 20 is filled with the contrast medium. Accordingly, it is possible to confirm an introduction position or a final expanded shape of the implant 20. Before the introduction of the filling material, the contrast medium is aspirated by an indeflator, a syringe, or the like, and is discharged from the inside of the implant 20.

Referring to FIGS. 7A and 7B, the implant 20 is caused to expand inside the living body 120 when the filling material is fed into the tubular member 83 such that the implant 20 starts to expand and is transformed. At this time, the second surface portion 24 of the folded implant 20 gradually moves to the front surface side from a state where the second surface portion 24 is covered with the first surface portion 23 and positioned on the inner side of the first surface portion 23. If the second surface portion 24 moves to the front surface side of the implant 20, the covering material m covered with the second surface portion 24 comes into contact with the body fluid, thereby increasing the friction coefficient. Therefore, when the filling material is injected to the implant 20 which indwells in the living body, the implant 20 expands without being displaced from the indwelling position. In addition, the covering material m covers only the second surface portion 24 of the implant 20. Accordingly, the first surface portion 23 and the second surface portion 24 do not adhere to each other. Therefore, the implant 20 smoothly expands.

Referring to FIGS. 7B and 8A, the tubular member 83 is separated from the implant 20. Thereafter, the outer cylinder 96 of the puncture member is removed from the living body 120. The implant 20 is thus indwelled between the spinous processes 123, and is used as a spacer for holding the distance between the spinous processes 123.

Referring to FIGS. 8A and 8B, the filling material which fills the implant 20 can maintain an expanded shape of the implant 20 for a long period of time.

As described above, according to the present embodiment, the implant assembly 10 includes the implant 20 and the guiding means 30. At least a portion on the surface of the implant 20 is covered with the covering material m whose friction coefficient increases by coming into contact with the liquid. Therefore, the covering material m on the surface of the implant 20 and the body fluid come into contact with each other inside the living body, thereby increasing the frictional coefficient. Accordingly, it is possible to smoothly expand the implant 20 without causing the implant 20 to be displaced from a predetermined indwelling position, when the filling material is injected. The guiding means 30 prevents the implant 20 and the body fluid of the living body from coming into contact with each other inside the living body, and guides the implant 20 to move to the indwelling position inside the living body. Therefore, it is possible to prevent an increase in the friction coefficient of the covering material m on the surface of the implant 20 while the implant 20 moves to the indwelling position. In this manner, the implant 20 can be smoothly introduced into the living body.

In addition, as described above, the surface of the implant 20 in the folded and contracted state is configured so that only the second surface portion 24, which is covered with the first surface portion 23 exposed outward so as to be positioned on the inner side of the first surface portion 23, is covered with the covering material m. Accordingly, while the body fluid is likely to permeate into the guiding means 30 when the implant 20 moves to the indwelling position, it is possible to preferably prevent the covering material m and the body fluid from coming into contact with each other. Therefore, it is possible to prevent an increase in the friction coefficient of the covering material m on the surface of the implant 20 while the implant 20 moves to the indwelling position. In this manner, the implant 20 can be smoothly introduced into the living body.

In addition, as described above, it is possible to use the implant assembly 10 to indwell a site between bones, a site between cartilages, a site inside the cartilage, or a site inside the bone in the living body, and which is easily introduced into the living body without any positional displacement.

Figure 9:
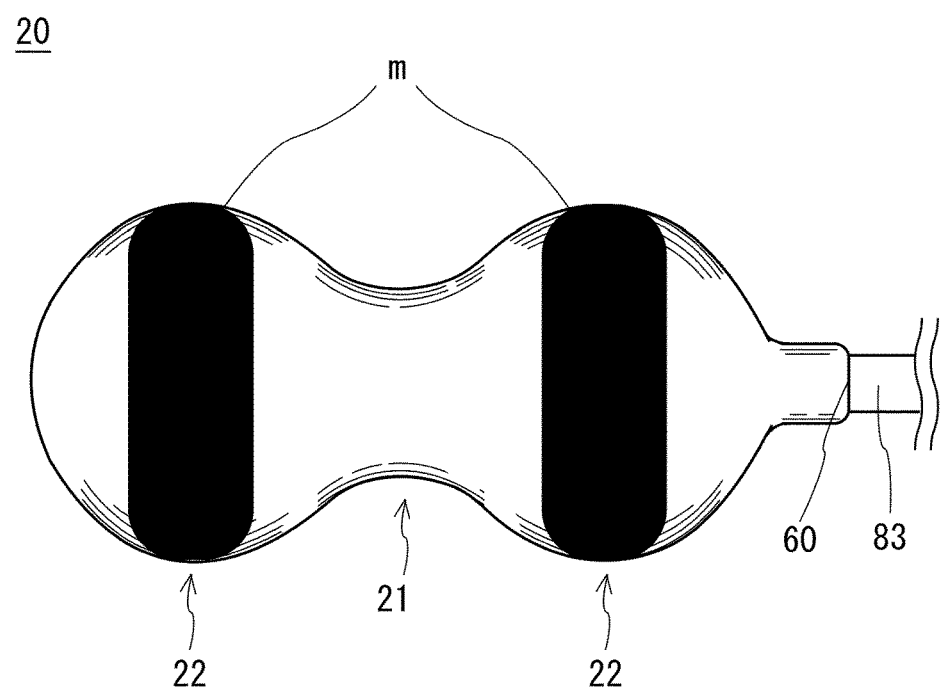
FIG. 9 is a view illustrating a modified example of a covering position of a covering material which covers a surface of the implant according to the disclosure.

Next, referring to FIG. 9, a modified example of a covering position of the covering material m which covers the surface of the implant 20 according to the disclosure herein will be described. The same reference numerals are given to members which are the same as those in the above-described first exemplary embodiment, and repeated description thereof will be omitted.

According to the modified example, the implant 20 has the body section 21 which extends in the longitudinal direction, and the wide section 22 which is disposed at both ends of the body section 21 and in which the width in the direction intersecting the longitudinal direction is larger than that of the body section 21 in a state after the implant 20 expands. The covering material m is disposed in only the wide section 22. Since the implant 20 has this shape, if the covering material m is disposed on at least the surface of the wide section 22 in which a variation amount thereof is largest and an area in contact with the living body is largest before and after the implant 20 is expanded and transformed, it is possible to prevent the implant 20 from being displaced from the predetermined indwelling position when the filling material is injected. As illustrated in FIG. 9, the covering material m is disposed on the entire circumference of the wide section 22 of the implant 20. Therefore, the covering material m covering the entire circumference of the wide section 22 and the body fluid come into contact with each other, thereby increasing the friction coefficient of the covering material m. Accordingly, the implant 20 smoothly expands without being displaced from the predetermined indwelling position.

In the modified example, a configuration has been described in which the covering material m covers only the wide section 22 of the implant 20. However, without being limited thereto, a configuration may be adopted in which the covering material m covers a surface corresponding to the second surface portion 24 of the implant 20 within the wide section 22 of the implant 20. According to this configuration, when the body fluid is likely to permeate into the guiding means 30 while the implant 20 moves to the indwelling position, it is possible to preferably prevent the covering material m and the body fluid from coming into contact with each other. Therefore, it is possible to prevent an increase in the friction coefficient of the covering material m on the surface of the implant 20 while the implant 20 moves to the indwelling position. In this manner, the implant 20 can be smoothly introduced into the living body.

As described above, according to the modified example, the implant 20 includes the body section 21 which extends in the longitudinal direction, and the wide section 22 which is disposed at both ends of the body section 21 and in which the width in the direction intersecting the longitudinal direction is larger than that of the body section 21 in a state after the implant 20 expands. Since the implant has this shape, the covering material m is disposed in at least the wide section 22 in which a variation amount thereof is largest and an area in contact with the living body is largest before and after the implant 20 is expanded and transformed. Therefore, it is possible to prevent the implant 20 from being displaced from the predetermined indwelling position when the filling material is injected.

Next, referring to FIG. 10, a second exemplary embodiment of the disclosure will be described. The same reference numerals are given to members which are the same as those in the above-described first embodiment, and repeated description thereof will be omitted.

According to the second embodiment, friction reducing means 40 for reducing the friction between the implant 20 and guiding means 230 is disposed in at least a portion on an inner surface of the guiding means 230. An implant assembly 210 is different from the implant assembly 10 according to the first exemplary embodiment in that this friction reducing means 40 is disposed on the inner surface of the guiding means 230.

The guiding means 230 includes a lumen 231 into which the implant 20 can be inserted, and the friction reducing means 40 for reducing the friction between the implant 20 and the guiding means 230. The friction reducing means is disposed in at least a portion of the inner surface of the guiding means 230 which is formed by the lumen 231. The friction reducing means 40 is configured so that the inner surface of the guiding means 230 is formed in an uneven shape. The uneven shape is formed on the inner surface of the guiding means 230, thereby forming a groove 41 on the inner surface of the guiding means 230.

The groove 41 is formed on the inner surface of the guiding means 230 in order to decrease a contact area when the implant 20 comes into contact with the inner surface of the guiding means 230. This groove 41 is disposed so as to decrease the contact area between the implant and the guiding means. Accordingly, the implant 20 can be smoothly introduced into the living body.

In addition, the groove 41 is formed on the inner surface of the guiding means 230 in order to evacuate the body liquid, when the body fluid permeates the inner surface through the open distal end of the guiding means 230. The groove 41 is formed on the inner surface of the guiding means 230 so as to define a predetermined length from the open distal end of the guiding means 230. The groove 41 prevents the friction coefficient from increasing due to the reaction between the body fluid and the covering material m covering the surface of the implant 20 while the implant 20 moves to the indwelling position inside the living body. Therefore, the implant 20 is not hindered from being introduced into the living body by the guiding means 230 having the groove 41 formed on the inner surface thereof, and thus the implant 20 can be smoothly introduced into the living body.

An absorber 50 which can absorb the body fluid is disposed in the recessed groove 41 formed on the inner surface of the guiding means 230.

The absorber 50 is disposed in a bottom portion of the groove 41 in order to hold the body fluid evacuated into the groove 41. The absorber 50 absorbs the body fluid evacuated into the groove 41 when the body fluid permeates the inner surface of the guiding means 230. Accordingly, the absorber 50 prevents the friction coefficient from increasing due to the reaction between the body fluid and the covering material m covering the surface of the implant 20 while the implant 20 moves to the indwelling position inside the living body. Therefore, the guiding means 230 in which the absorber 50 is disposed in at least a portion inside the groove 41 can smoothly introduce the implant 20 into the living body.

As the absorber 50, for example, it is possible to use water-absorbing polymers such as an acrylic acid polymer and the like, polymerized resins of water soluble monomers such as polyacrylamide, polyvinyl alcohol, polyethylene glycol, and the like, or acrylonitrile polymer compounds.

As described above, according to the second exemplary embodiment, the friction reducing means 40 is disposed on the inner surface of the guiding means 230, thereby reducing the friction between the implant 20 and the guiding means 230. In this manner, the implant 20 can be smoothly introduced into the living body.

In addition, as described above, the inner surface of the guiding means 230 is formed in the uneven shape, thereby decreasing the contact area between the implant 20 and the guiding means 230. Accordingly, the implant 20 can be smoothly introduced into the living body. In addition, even when the body fluid is likely to permeate into the inner surface of the guiding means 230, the body fluid can be evacuated into the recessed groove 41. Accordingly, it is possible to prevent the covering material m on the surface of the implant 20 and the body fluid from coming into contact with each other, when the implant 20 moves to the indwelling position inside the living body. Therefore, it is possible to prevent an increase in the friction coefficient of the covering material m on the surface of the implant 20 while the implant 20 moves to the indwelling position. In this manner, the implant 20 can be smoothly introduced into the living body.

In addition, as described above, the absorber 50 which can absorb the body fluid is disposed inside the recessed groove 41 formed on the inner surface of the guiding means 230. Accordingly, it is possible to hold the body fluid evacuated into the groove 41. Therefore, it is possible to more reliably prevent the covering material m on the surface of the implant 20 and the body fluid from coming into contact with each other when the implant 20 moves to the indwelling position inside the living body. Therefore, it is possible to more reliably prevent an increase in the friction coefficient of the covering material m on the surface of the implant 20 while the implant 20 moves to the indwelling position. In this manner, the implant 20 can be smoothly introduced into the living body.

Figure 11:
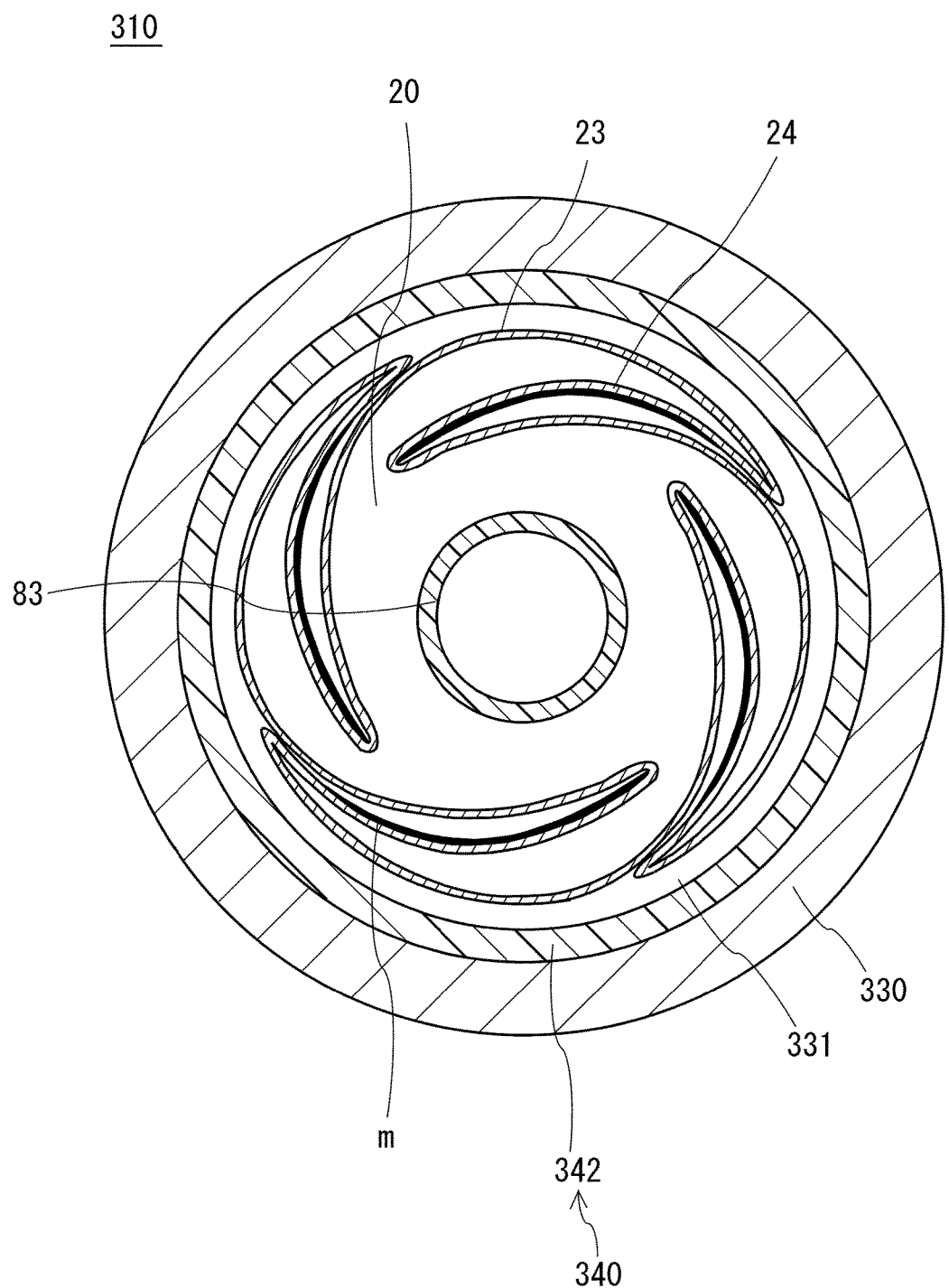
FIG. 11 is a schematic view for describing an implant assembly according to a third embodiment of the disclosure.

Next, referring to FIG. 11, a third exemplary embodiment will be described. The same reference numerals are given to members which are the same as those in the above-described first and second embodiments, and repeated description thereof will be omitted.

According to the third embodiment, friction reducing means 340 has a low friction member 342. An implant assembly 310 is different from the implant assembly 210 according to the second embodiment in that the friction reducing means 340 disposed on an inner surface of guiding means 330 has a different configuration.

The friction reducing means 340 is configured to include the low friction member 342 which covers the inner surface of the guiding means 330.

The low friction member 342 is a covering layer which covers the inner surface of the guiding means 330, and is configured to have a highly water-repellent material. The low friction member 342 is highly water-repellent. Accordingly, the body fluid is repelled when the body fluid permeates the inner surface of the guiding means 330, while the implant 20 is moved to the indwelling position by the guiding means 330. In this manner, the body fluid is prevented from permeating the inner surface through the open distal end of the guiding means 330. Therefore, the low friction member 342 can prevent the friction coefficient from increasing due to the reaction between the body fluid and the covering material m covering the surface of the implant 20 while the implant 20 moves to the indwelling position inside the living body.

As the low friction member 342, for example, it is possible to use fluorine-based polymers such as Teflon and the like, paraxylylene-based polymers such as parylene and the like, lubricious polymers such as polyethylene oxide and the like, amorphous carbon such as diamond-like carbon and the like, silicon oil, or the like. The material of the low friction member 342 is not particularly limited, and can be appropriately changed as long as the material prevents an increase in the friction coefficient between the surface of the implant 20 and the inner surface of the guiding means 330.

The guiding means 330 has a lumen 331 into which the implant 20 can be inserted.

As described above, according to the third exemplary embodiment, the friction reducing means 340 is configured to include the low friction member 342 covering the inner surface of the guiding means 330, thereby more reliably reducing the friction between the implant 20 and the guiding means 330. Therefore, it is possible to prevent an increase in the friction coefficient of the covering material m on the surface of the implant 20 while the implant 20 moves to the indwelling position. In this manner, the implant 20 can be smoothly introduced into the living body.

As described above, according to the third embodiment, compared to the configuration according to the second embodiment, the friction reducing means 340 can be configured using a simpler configuration in which the inner surface of the guiding means 330 is covered with the covering layer (low friction member 342).

The above-described exemplary embodiments can be appropriately modified.

As the exemplary embodiments are described above, a configuration has been described in which the guiding means 30 also serves as the cylindrical portion 98 of the outer cylinder 96 of the puncture device 90. However, without being limited thereto, the guiding means 30 may be a member which is separate from the cylindrical portion 98 of the outer cylinder 96 of the puncture device 90.

As the embodiments are described above, a configuration has been described in which the groove 41 is formed on the inner surface of the guiding means 230 so as to define a predetermined length from the open distal end of the guiding means 30. However, without being limited thereto, a configuration may be adopted in which the groove 41 does not reach the open distal end of the guiding means 30 on the inner surface of the guiding means 230. According to this configuration, it is possible to prevent the body fluid from permeating the inner surface of the guiding means 30 through the open distal end of the guiding means 30 due to capillary action.

In addition, as the embodiments are described above, the groove 41 is disposed as the friction reducing means 40. However, without being limited thereto, the inner surface of the guiding means 30 may be processed so that the contact area between the implant 20 and the inner surface of the guiding means 30 decreases due to an uneven shape, a dimple (depressed) shape, an embossed (raised) shape, a projection shape, a grid shape, or the like, for example.

Figure 10:
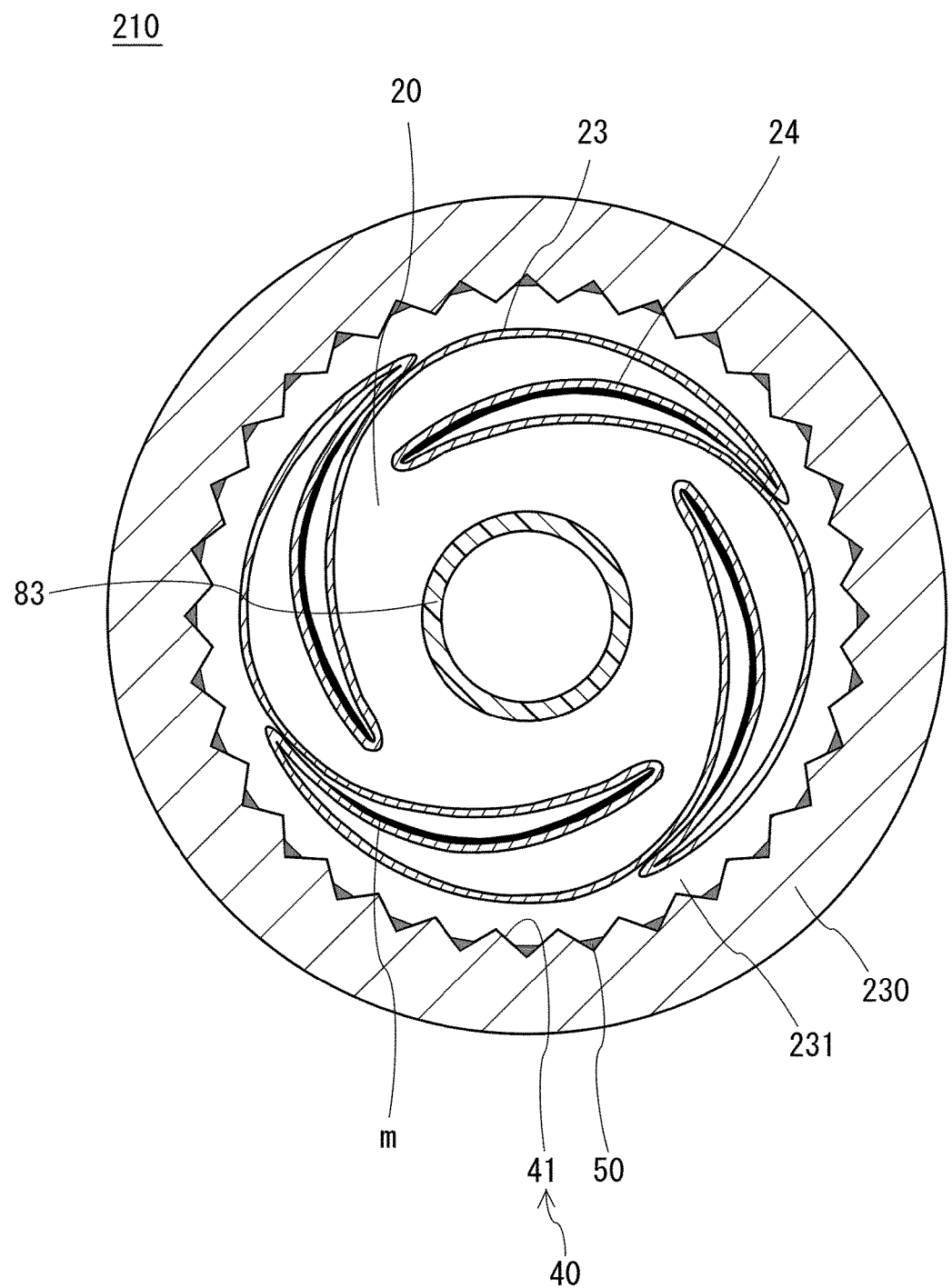
FIG. 10 is a schematic view for describing an implant assembly according to a second embodiment of the disclosure.

In addition, as the embodiments are described above, a configuration has been described in which the guide means 230 has the groove 41 and the absorber 50 as the friction reducing means 40 as illustrated in FIG. 10. However, without being limited thereto, a configuration may be adopted in which only the groove 41 is disposed therein, for example.

In addition, as the embodiments are described above, a method has been described in which the implant 20 is introduced into the living body 120 by the puncture device 90 including the inner needle 91 and the outer cylinder 96. However, the method of introducing the implant 20 is not limited thereto. The method can be appropriately changed as long as the implant 20 can be introduced into a predetermined site inside the living body. For example, a method can be employed in which the living body is punctured and the implant is introduced in a single step by using a puncture needle or the like which includes a body section to which the implant can be inserted and which can hold the implant.

The implant 20 can show an advantageous effect in that a load to the living body can be reduced when only the implant 20 is caused to indwell in the living body. Therefore, without using the implant assembly 10 combined with the tubular member 83 as described in the embodiments, only the implant 20 can be used for manual implantation.

The detailed description above describes an implant assembly. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An implant assembly comprising:
an implant configured to be transformable from a folded and contracted state to an expanded state by an introduced filling material, at least a portion of a surface thereof is covered with a covering material whose friction coefficient is configured to increase by coming into contact with a body fluid; and
guiding means for preventing the implant and the body fluid of a living body from coming into contact with each other inside the living body, and for guiding the implant to move to an indwelling position inside the living body;
wherein, when the implant is in the folded and contracted state, the covering material is covered by a folded portion of the implant and the implant has a first friction coefficient, and
wherein, when the implant is expanded to the expanded state, the covering material is exposed on an outer surface of the implant and the implant has a second friction coefficient, the second friction coefficient being greater than the first friction coefficient.

2. The implant assembly according to claim 1, wherein a first surface portion which is exposed outward and a second surface portion, which is covered with the first surface portion so as to be positioned on an inner side of the first surface portion, are formed on a surface of the implant in the folded and contracted state, and wherein the covering material covers only the second surface portion.

3. The implant assembly according to claim 1, wherein the implant has a body section which extends in a longitudinal direction, and a wide section disposed at both ends of the body section and whose width in a direction intersecting the longitudinal direction is greater than the width of the body section in a state after the implant expands, and wherein the covering material is disposed on only the wide section.

4. The implant assembly according to claim 1, wherein the guiding means has a lumen into which the implant can be inserted, and friction reducing means for reducing friction between the lumen and the implant disposed on at least a portion of an inner surface of the guiding means which is formed by the lumen.

5. The implant assembly according to claim 4, wherein the friction reducing means is configured so that the inner surface of the guiding means is formed in an uneven shape.

6. The implant assembly according to claim 5, wherein the uneven shape includes a recessed groove and wherein an absorber which can absorb the body fluid is disposed inside a recessed groove formed on the inner surface of the guiding means.

7. The implant assembly according to claim 4, wherein the friction reducing means is configured to include a low friction member which covers the inner surface of the guiding means.

8. The implant assembly according to claim 1, wherein the implant is used in order to expand a site between bones, a site between cartilages, a site inside the cartilage, or a site inside the bone in the living body.

9. The implant assembly according to claim 1, wherein the implant has a dumbbell shape in the expanded state.

10. The implant assembly according to claim 1, further comprising a puncture device for introducing the implant into the living body, the puncture device including an inner needle configured to puncture the living body and an outer cylinder from which the inner needle can be inserted and removed.

11. The implant assembly according to claim 10, wherein the guiding means includes a cylindrical portion having an open distal end.

12. The implant assembly according to claim 1, wherein the implant includes an introduction port through which the filling material is introduced.

13. The implant assembly according to claim 1, wherein the covering material includes natural products, chemically modified natural products, synthetic products or a mixture of two or more types of products.

14. The implant assembly according to claim 13, wherein the covering material further includes at least one of a compatible liquid plasticizer and a filling material.

15. The implant assembly according to claim 1, wherein the filling material includes a curing material.

16. An implant assembly comprising:
an implant configured to be transformable from a folded and contracted state to an expanded state by an introduced filling material, at least a portion of a surface thereof is covered with a covering material whose friction coefficient increases by coming into contact with a body fluid; and
guiding means for preventing the implant and the body fluid of a living body from coming into contact with each other inside the living body, and for guiding the implant to move to an indwelling position inside the living body;
wherein the guiding means has a lumen into which the implant can be inserted, and friction reducing means for reducing friction between the lumen and the implant disposed on at least a portion of an inner surface of the guiding means which is formed by the lumen;
wherein the friction reducing means is configured so that the inner surface of the guiding means is formed in an uneven shape; and
wherein the uneven shape includes a recessed groove and wherein an absorber which can absorb the body fluid is disposed inside a recessed groove formed on the inner surface of the guiding means.

17. The implant assembly according to claim 16,
wherein the friction reducing means is configured to include a low friction member which covers the inner surface of the guiding means.

18. The implant assembly according to claim 16, further comprising a puncture device for introducing the implant into the living body, the puncture device including an inner needle which punctures the living body and an outer cylinder from which the inner needle can be inserted and removed.

19. The implant assembly according to claim 16, wherein the covering material includes natural products, chemically modified natural products, synthetic products or a mixture of two or more types of products.

\* \* \* \* \*